(12) United States Patent
Pretorius

(10) Patent No.: US 9,778,227 B2
(45) Date of Patent: Oct. 3, 2017

(54) DEVICE AND SYSTEM FOR AND A METHOD OF MONITORING A CABLE FOR A PHYSICAL DISTURBANCE

(71) Applicant: Ernst Jacobus Gustav Pretorius, Pretoria (ZA)

(72) Inventor: Ernst Jacobus Gustav Pretorius, Pretoria (ZA)

( * ) Notice: Subject to any disclaimer, the term of this patent is extended or adjusted under 35 U.S.C. 154(b) by 248 days.

(21) Appl. No.: 14/651,846

(22) PCT Filed: Dec. 12, 2013

(86) PCT No.: PCT/IB2013/060835
§ 371 (c)(1),
(2) Date: Jun. 12, 2015

(87) PCT Pub. No.: WO2014/091434
PCT Pub. Date: Jun. 19, 2014

(65) Prior Publication Data
US 2015/0338379 A1 Nov. 26, 2015

(30) Foreign Application Priority Data

Dec. 12, 2012 (ZA) .................................. 2012/09444

(51) Int. Cl.
*G01N 29/04* (2006.01)
*G01N 29/24* (2006.01)
(Continued)

(52) U.S. Cl.
CPC .............. *G01N 29/04* (2013.01); *G01H 1/00* (2013.01); *G01H 3/00* (2013.01); *G01N 29/14* (2013.01); *G01N 29/2437* (2013.01)

(58) Field of Classification Search
CPC ........ G01N 29/04; G01N 29/14; G01N 29/38; G01N 29/46; G01H 1/00
See application file for complete search history.

(56) References Cited

U.S. PATENT DOCUMENTS 2,345,771 A * 4/1944 Reynolds ............. G08B 13/122
340/566
3,713,127 A * 1/1973 Keledy .................. G01N 29/14
340/540
(Continued)

FOREIGN PATENT DOCUMENTS

CN          2067413 U       12/1990
DE      102010041715 A1      4/2012
(Continued)

OTHER PUBLICATIONS

International Search Report prepared by the Austrian Patent Office dated Jun. 12, 2014, for International Application No. PCT/IB2013/060835.

*Primary Examiner* — Helen Kwok
(74) *Attorney, Agent, or Firm* — Sheridan Ross P.C.

(57) ABSTRACT

A device, system and method for monitoring a cable for a physical disturbance is disclosed. The device includes at least one pair of acoustic transducers, the pair comprising a first acoustic conductor monitoring transducer and a second ambient transducer. The acoustic conductor monitoring transducer is in acoustic contact with an acoustic conductor to be monitored by the device, with the transducers being arranged such that an ambient acoustic signal is common to both transducers. The device further includes a circuit element, with each transducer being connected to an input of the circuit element, the circuit element being arranged to output a difference between the input signals from the transducers. An alarm triggering module is connected to an output of the circuit element, the module being operable to trigger an alarm when the output signal received from the circuit element exceeds a predefined threshold value.

19 Claims, 4 Drawing Sheets

(51) Int. Cl.
*G01N 29/14* (2006.01)
*G01H 1/00* (2006.01)
*G01H 3/00* (2006.01)

(56) References Cited

U.S. PATENT DOCUMENTS

| | | | | |
|---|---|---|---|---|
| 3,803,548 A * | 4/1974 | Skujins, Jr. | ............ | G08B 13/169 340/566 |
| 4,005,363 A * | 1/1977 | Mifflin | ............ | G01R 31/11 324/525 |
| 4,197,529 A * | 4/1980 | Ramstedt | ............ | G08B 13/26 174/102 R |
| 4,386,343 A * | 5/1983 | Shiveley | ............ | G08B 13/1672 340/515 |
| 4,481,818 A * | 11/1984 | Hellqvist | ............ | G01S 5/22 73/587 |
| 4,565,964 A * | 1/1986 | Matthews | ............ | G01S 15/88 324/536 |
| 4,609,994 A * | 9/1986 | Bassim | ............ | G01N 29/14 702/39 |
| 4,747,309 A * | 5/1988 | Weir | ............ | G01M 3/24 340/555 |
| 5,251,469 A | 10/1993 | Chan | | |
| 5,268,672 A * | 12/1993 | Kerr | ............ | G08B 13/169 340/565 |
| 5,457,994 A * | 10/1995 | Kwun | ............ | G01N 29/14 73/587 |
| 5,798,457 A * | 8/1998 | Paulson | ............ | E04C 5/08 73/587 |
| 6,082,193 A * | 7/2000 | Paulson | ............ | G01M 3/243 73/152.58 |
| 7,202,797 B2 * | 4/2007 | Zhavi | ............ | B61L 1/06 340/566 |
| 7,423,931 B2 * | 9/2008 | Martin, II | ............ | H04B 13/00 340/870.01 |
| 7,607,351 B2 * | 10/2009 | Allison | ............ | F16L 55/00 702/36 |
| 8,195,409 B2 * | 6/2012 | Bruno | ............ | G01S 3/801 702/56 |

FOREIGN PATENT DOCUMENTS

WO    WO 9825121 A1    6/1998
WO    WO 0188658 A2    11/2001

* cited by examiner

DEVICE AND SYSTEM FOR AND A METHOD OF MONITORING A CABLE FOR A PHYSICAL DISTURBANCE

CROSS REFERENCE TO RELATED APPLICATIONS

This application is a national stage application under 35 U.S.C. 371 and claims the benefit of PCT Application No. PCT/IB2013/060835 having an international filing date of Dec. 12, 2013, which designated the United States, which PCT application claimed the benefit of South Africa Application No. ZA 2012/09444 filed Dec. 12, 2012, the disclosure of each of which are incorporated herein by reference.

FIELD OF INVENTION

This invention relates to the security industry and in particular to a device, system and method of monitoring a cable in order to detect when intrusion, theft or tampering with the cable occurs.

BACKGROUND OF INVENTION

The theft of livestock and of electrical power cables is a problem which many people have attempted to address with little, to limited success. Electric fences are generally effective in preventing trespassing. However, a downside of an electric fence is the burden and cost of erecting a new fence with insulators or bobbins as well as the cost of installing an energiser. Known cable monitors, such as reflectometers transmit electromagnetic waves along a cable while measuring reflections in order to establish when a change of impedance has occurred which could be associated with severing or illegal tapping of power from an electrical power cable. Although such reflectometers can successfully detect when a cable is cut, they are difficult to install, complex instruments that require technical expertise, and are quite expensive.

The Inventor desires a device, system and method which at least alleviates some of the drawbacks discussed above.

SUMMARY OF INVENTION

According to a first aspect of the invention, there is provided a device for monitoring an acoustic conductor for a physical disturbance, the device including:
  at least one pair of acoustic transducers, the pair comprising a first acoustic conductor monitoring transducer and a second ambient transducer, the acoustic conductor monitoring transducer operatively being in acoustic contact with an acoustic conductor to be monitored by the device, the transducers being arranged such that an ambient acoustic signal is common to both transducers;
  a circuit element, with each transducer being connected to an input of the circuit element, the circuit element being arranged to output a difference between the input signals from the transducers; and
  an alarm triggering module which is connected to an output of the circuit element, the module being operable to trigger an alarm when the output signal received from the circuit element exceeds a predefined threshold value.

In an embodiment, the acoustic conductor comprises a cable.

The device may include a coupler which operatively connects the cable to be monitored to, or brings the cable in abutment with, the cable monitoring transducer such that a mechanical wave or vibration in the cable is transferred or conveyed to the transducer.

In one version, each cable has a device fitted thereto with the coupler. Alternatively, one device may be arranged to monitor a plurality of cables, in which the cable monitoring transducer in the device is connected to the plurality of cables with a plurality of couplers.

The coupler is typically of a solid material which has better mechanical wave propagation properties than air, for example.

The circuit element may comprise a differential amplifying circuit element, wherein each transducer is connected to an input of the circuit element, which is configured to cancel a signal common to the inputs thus amplifying and outputting a difference between the signals input to the circuit element.

The circuit element may be in the form of a differential amplifier. The acoustic transducers may be arranged in close proximity to each other to ensure that the ambient acoustic signal is common to both transducers. The acoustic transducers are operable to convert an acoustic signal, for example a physical vibration or pressure wave into an electrical voltage, irrespective of the phase of a medium the acoustic signal is travelling in. Understandably, the phase of the medium may be liquid, solid or gas or any combination of the above. Preferably, the medium is a solid or gas.

The device may include further circuitry such as a high pass filter connected between each transducer and an input to the circuit element. The high pass filter removes any DC components from the signal received from the transducers.

In a fairly basic embodiment of the device, the alarm triggering module may include at least one comparator having a predefined threshold voltage as one input to the comparator and the output of the circuit element as the other input. When the output received from the circuit element exceeds the threshold voltage, the comparator is configured to trigger an alarm. The alarm triggering module may include delay circuitry which is configured to maintain the output of the circuit element for a short period.

In a more sophisticated embodiment, the alarm triggering module may include an analogue-to-digital converter (A/D) and a processor which is operable to compute, based on a level of the output received from the circuit element, whether or not the alarm should be triggered and to trigger the alarm depending on the outcome of the computation. The processor may be a digital signal processor (DSP) or microprocessor.

The device may further include a communication module connected to the alarm triggering module, the communication module being operable to communicate with a remote monitoring station or other suitable device. The communication module may be a wireless communication module.

The acoustic transducers may be in the form of microphones. Alternatively, the acoustic transducers may be in the form of piezoelectric transducers. The acoustic conductor monitoring transducer may be configured to be arranged in direct mechanical contact with the acoustic conductor being monitored. In this way the sensitivity of the device can be improved because attenuation of the physical disturbance is minimised.

The cable may be an electrified cable and the device may accordingly be resistant to electrical shock.

In an embodiment, the device includes a pair of acoustic conductor monitoring transducers and a pair of ambient transducers, wherein the pair of acoustic conductor monitoring transducers are spaced one wavelength (1λ) apart from each other and/or the pair of ambient transducers are spaced one wavelength (1λ) apart from each other, to reinforce these signals, and the pair of acoustic conductor monitoring transducers and the pair of ambient transducers are spaced a half wavelength (½λ) apart from each other, to cancel the common signals between the monitoring transducers and the ambient transducers. In this embodiment, the circuit element comprises an amplifier to amplify the resulting differential signal.

In a similar arrangement, when using piezoelectric transducers in particular, the piezoelectric transducers may be connected together so as to reinforce the signals from the monitoring transducers and/or ambient transducers, and to cancel the common signals between the monitoring transducers and ambient transducers, with the circuit element comprising an amplifier to amplify the resulting differential signal.

In an alternate envisaged application, the acoustic conductor comprises the ground, in which case the device is fitted to a peg inserted into the ground, with the acoustic conductor monitoring transducer being in acoustic contact with the ground in order to determine whether someone is digging a hole in the ground.

In yet a further envisaged embodiment, the acoustic conductor comprises an irrigation pipe.

The invention extends to a method of monitoring a cable for a physical disturbance, the method including:
placing a first acoustic transducer in acoustic contact with a cable to be monitored and measuring using the first acoustic transducer an acoustic signal associated with the cable;
using the first acoustic transducer and a second acoustic transducer, simultaneously measuring an ambient acoustic signal which is common to the first and second acoustic transducers;
cancelling using a circuit element the ambient acoustic signal which is common to the first and second transducers in order to amplify a difference between the signals of the first and second acoustic transducers respectively; and
triggering using an alarm triggering module an alarm or warning signal when an output signal received from the circuit element exceeds a predefined threshold value.

Triggering may include communicating via a communication module over a communication network, the occurrence of an alarm triggering event to a remote station.

The invention extends to a system for monitoring an acoustic conductor for a physical disturbance, the system including:
at least one device for monitoring an acoustic conductor for a physical disturbance, the device including at least one pair of acoustic transducers, the pair comprising a first acoustic conductor monitoring transducer and a second ambient transducer, the acoustic conductor monitoring transducer operatively being in acoustic contact with the acoustic conductor to be monitored by way of a coupler such that the acoustic conductor monitoring transducer is able to measure an acoustic signal associated with the acoustic conductor, the transducers being arranged such that an ambient acoustic signal is common to both transducers, wherein the device is configured, through the use of circuitry, to output a difference between the input signals to the circuitry; and
a control module which is in communication with the device and which is configured to receive as input the output of the circuitry of the device, the control module being operable to determine, based on the input received from the device whether or not an alarm triggering event has occurred, and to trigger an alarm if need be.

The system may include a plurality of devices, each of which is operatively connected to a cable to be monitored for a physical disturbance. The devices may be connected to a single cable at spaced apart positions. Alternatively, or in addition, the devices may be connected to a number of separate cables or wires forming part of a fixed construction, such as a fence.

The device may be a device as described above.

The control module may be operable to receive as input the output of the circuitry of at least two separate devices. To this end, the control module may be operable to calculate the location of a physical disturbance measured between two devices connected to the same cable, the devices being a predetermined distance apart.

The system may include at least one apparatus which includes a device as described above. The apparatus may include a device and a control module as described above. The apparatus may further include a communication module.

The system may include a plurality of apparatus, each apparatus having a communication module enabling communication between the respective apparatus. The communication module may be a wireless communication module. The communication module may be operable to communicate with a remote station.

The system may include a power source. The power source may be in the form of a battery. The system may be operable to derive power from an electrical power source by way of, for example, capacitive coupling or induction coupling.

The wireless communication module may be a radio frequency communication module. The system may include a strain gauge which is operable to convert a change in tension of a cable into an acoustic signal which can be detected by the system.

The system may include a remote monitoring station in the form of a handheld unit comprising a GPS, the device further including a communication module which is configured to communicate with the handheld unit and to forward a notification message to the handheld unit in the event that the alarm is triggered.

The device may include a tilt sensor which is activated when the device is tilted. This may serve as a warning that the device is being tampered with. Alternatively, or in addition, the device may include a tamper sensor to detect when someone attempts to sabotage the device. The device may include a watertight housing which houses the circuitry. The device may further include a temperature sensor which is configured to detect when the temperature of the device rises above a predefined threshold as in the case of a fire.

The system may further include a remote controlled unmanned aircraft which includes a surveillance camera. The aircraft can be flown out to the point where an alarm has been detected in order to survey the surroundings. In the event that the GPS coordinates are available for the point where the alarm was triggered, the aircraft may be configured automatically to fly out to the point where the disturbance was detected and perform surveillance.

BRIEF DESCRIPTION OF DRAWINGS

The invention will now be further described, by way of example, with reference to the accompanying schematic drawings.

In the drawings.

DETAILED DESCRIPTION OF AN EXAMPLE EMBODIMENT

Figure 1:
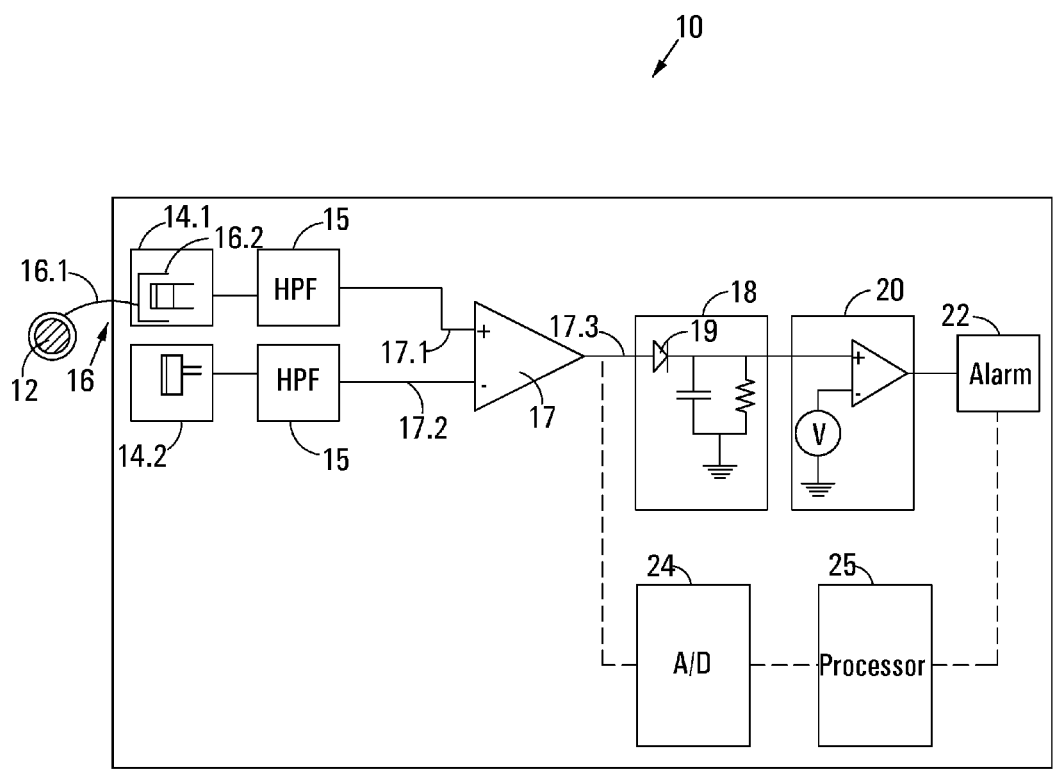
FIG. 1 illustrates a schematic block diagram of a device in accordance with the invention.

In the figures, reference numeral 10 refers generally to a device in accordance with the invention for monitoring a cable 12 for a physical disturbance.

The device 10 includes a pair of acoustic transducers in the form of microphones 14 which are arranged in close proximity to each other. The pair of microphones 14 comprises a cable monitoring microphone 14.1 and an ambient noise cancelling microphone 14.2. The cable monitoring microphone 14.1 is coupled or linked to the cable 12 being monitored for a physical disturbance by a coupler 16. The coupler 16 is in the form of a piece of wire 16.1, one end of which is wound around the cable 12. In one version, the end of the wire 16.1 may be crimped onto the cable 12 using a suitably designed pair of pliers.

Alternatively, the acoustic transducers may be in the form of piezoelectric transducers. In the case of piezoelectric transducers, which are preferred, the wire 16 may be attached in direct physical contact with the transducer in order to minimise attenuation of any physical disturbances to be sensed by the transducer. Furthermore, the piezoelectric transducers may be isolated from vibration transferred to the transducers via a housing of the device 10 using vibration mounts.

The coupler 16 includes a cap 16.2 attached to an opposite end of the wire 16.1. The cap 16.2 is partially received over the cable monitoring microphone 14.1 and is closely spaced from or in abutment with a diaphragm of the cable monitoring microphone 14.1 such that any mechanical wave or physical disturbance, for example vibration in the cable 12, is transferred to the microphone 14.1. The coupler 16 ensures that the same acoustic signal or physical disturbance conveyed to the cable monitoring microphone 14.1 is not conveyed to the noise cancelling microphone 14.2.

The cable 12 to be monitored may be any cable, wire or perimeter enclosure irrespective of its mechanical properties. The cable 12 must be tensioned to a certain degree, however, in order to facilitate mechanical wave propagation along the cable 12. Both unshielded and shielded or insulated cables can be monitored using the device 10.

The microphones 14 convert acoustic or mechanical waves into electrical voltages. Hence two channels 17.1, 17.2 carrying two electrical voltage signals are present in the device 10, one signal originating from each microphone 14. The electrical voltage signal received from each microphone 14.1, 14.2 is passed through a high pass filter 15 to remove any direct current (DC) components present in the signal before the signals are input to a differential amplifier 17. The differential amplifier 17 cancels a common-mode signal which is common to both channels 17.1, 17.2 and amplifies a differential-mode signal. This amplified differential-mode signal is provided as output 17.3 of the amplifier 17. In this manner the device 10 isolates and emphasises acoustic or mechanical waves being propagated in the cable 12 only. Ambient noise is measured on both microphones 14.1, 14.2 and is therefore cancelled by the amplifier 17. Disturbances of the cable 12 are, however, measured on the cable monitoring microphone 14.1 only and are therefore present on channel 17.1 only and are amplified by the amplifier 17. The gain of the amplifier 17 may be adjusted according to the needs of any particular application of the device 10.

The output 17.3 of the amplifier 17 is passed through a delay circuit 18 which comprises a diode 19 and a parallel RC arrangement having a fixed time constant. A maximum voltage level output by the amplifier 17 is therefore maintained for a short period, depending on the time constant of the RC arrangement of the delay circuit 18 and passed onto a comparator 20 which follows upon the delay circuit 18. Provided the voltage level input to the comparator 20 from the delay circuit 18 exceeds a predetermined threshold voltage (Vref), then an alarm 22 is triggered.

The above configuration of the device 10, including the delay circuit 18 and comparator 20, is the most basic configuration of the device 10. In an alternative configuration shown in FIG. 1, the device includes an analogue-to-digital converter 24 which digitises the output 17.3 received from the differential amplifier 17 and a microprocessor 25 which is operable to compute whether an alarm triggering event has occurred and, in response thereto, to activate the alarm 22.

Figure 2:
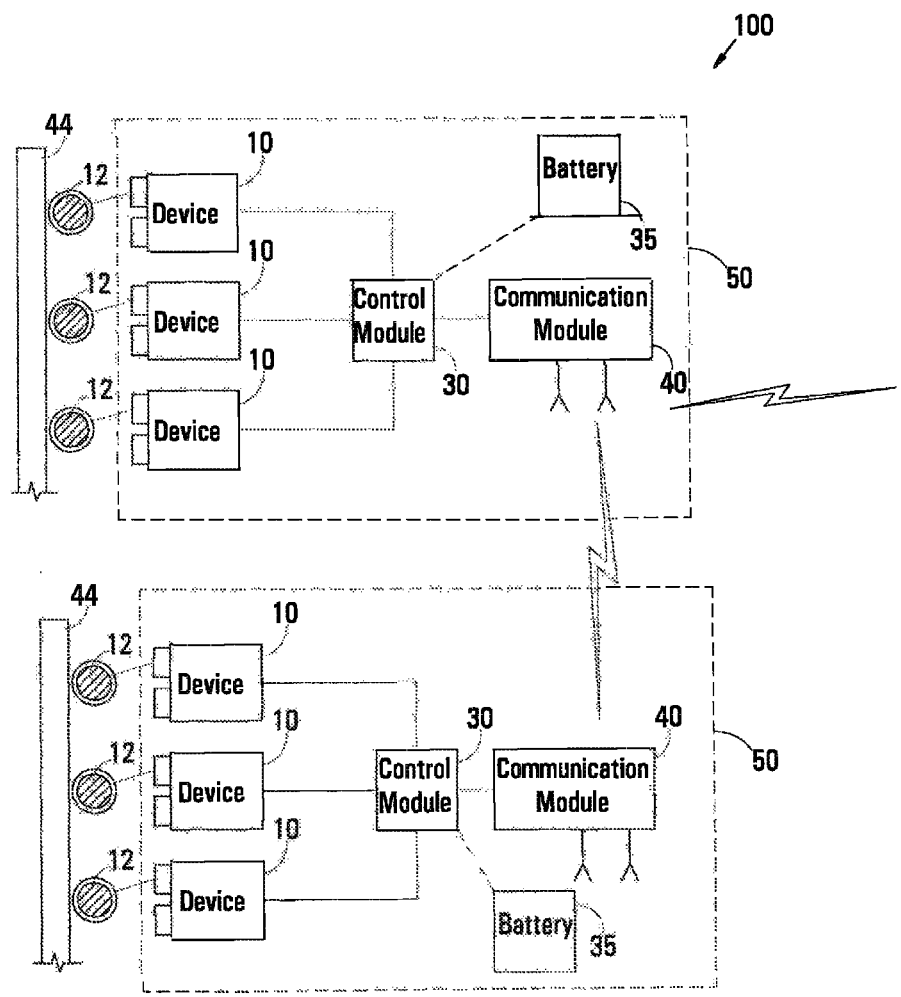
FIG. 2 shows a schematic block diagram of a system in accordance with the invention.

The invention extends to a system 100 for monitoring a plurality of cables 12 for intrusion or physical disturbances. The system 100 is schematically represented in FIG. 2. The system 100 includes at least two apparatus 50, each of which includes three devices 10 as described above. Each device 10 is coupled to a cable 12, as shown, and monitors the cable 12 for a physical disturbance. The apparatus 50 further includes a control module 30, a communication module 40 and a battery 35. The battery 35 is optional and could be replaced by an electrical connection to the power grid or in an alternative configuration (not shown) the apparatus 50 may be configured to derive power from the cable 12 where the cable 12 is a current/voltage carrying power cable by way of inductive/capacitive coupling.

Each of the devices 10, which are operable to sense a physical disturbance on the cables 12, are connected to the control module 30. The control module 30 is therefore operable to determine when an alarm triggering event has occurred and to sound the alarm in response thereto. The control module 30 may include a processor in the form of a digital signal processor (DSP). The control module 30 is operable to communicate with the communication module 40, which in turn is operable to communicate with the communication module 40 of the other apparatus 50. At least one of the communication modules 40 may be configured to communicate via a wireless network to a remote monitoring station.

Figure 3:
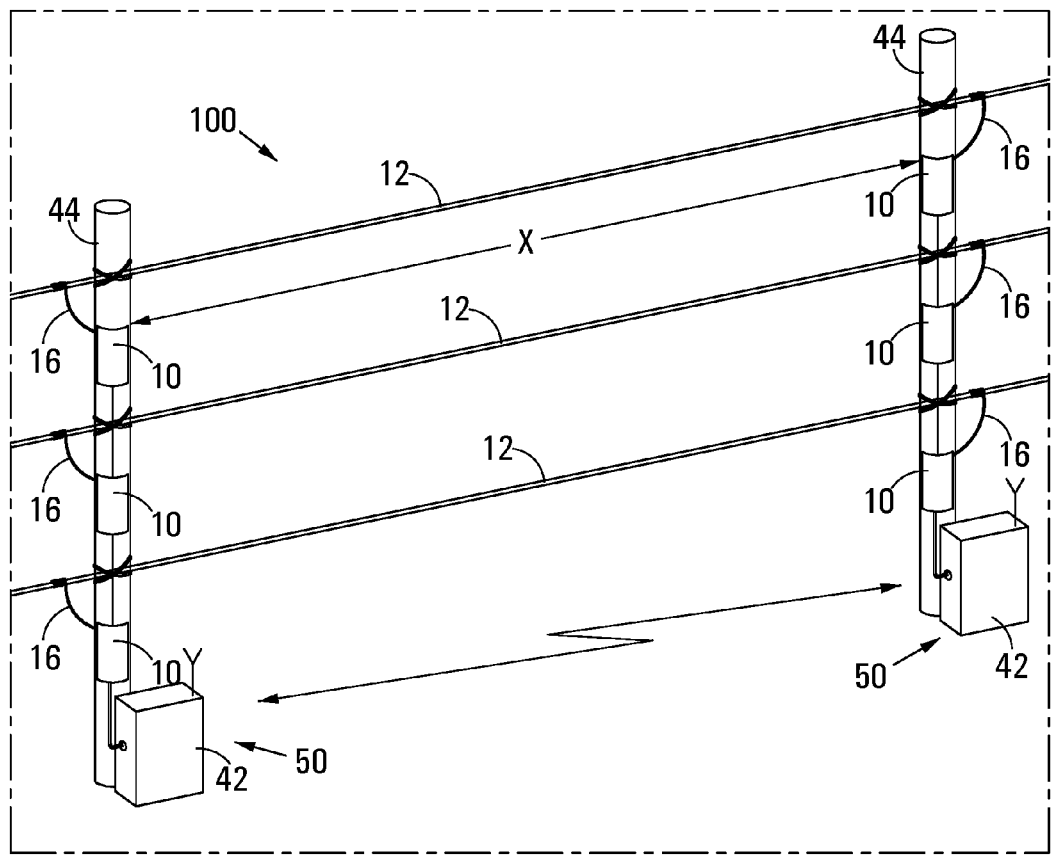
FIG. 3 shows a diagrammatic illustration of the system in accordance with a first embodiment of the invention.

A diagrammatic representation of the system 100 is shown in FIG. 3. In this example configuration, a device 10 has been mounted to a fence post 44 proximate each cable 12 to be monitored and coupled to the cable 12 by way of the coupler 16. An apparatus 50 is therefore provided at each post 44. The communication module 40, battery 35 and control module 30 of the apparatus 50 are housed in a housing 42 toward a base of the post 44. The apparatus 50 are operable to communicate with one another by way of the communication modules 40 which are in the form of wireless communication modules. Because a distance X between devices 10 of neighbouring apparatus 50 is known and the approximate speed of sound within a cable is known, the approximate location of a physical disturbance on the cable occurring between a pair of longitudinally spaced apart devices 10, monitoring a single cable 12, can be calculated by taking note of the difference in time elapsed for the acoustic disturbance to travel to the respective devices 10. Such calculations can be performed by the control module 30. Details of the elapsed time for the disturbance to reach the respective devices 10 can be communicated between the apparatus 50 via the communication modules 40.

Depending on a sensitivity of the devices 10 and a common mode rejection ratio (CMRR) of the differential amplifiers 17, the devices 10 can be spaced apart as required. It is believed that a range of up to 2 kilometers between devices 10 can be achieved in favourable conditions.

Furthermore, it is anticipated that it may be possible to prevent false alarms caused by ordinary disturbances of the cable 12 such as wind, rain, hail and the like which act upon the cable by characterising the frequency responses of such disturbances and rejecting them using the control module 30 when they occur. Consequently it may also be possible to characterise the frequency response caused when the cable is cut, the control module 30 being operable to identify such a response and to trigger the alarm.

Figure 4:
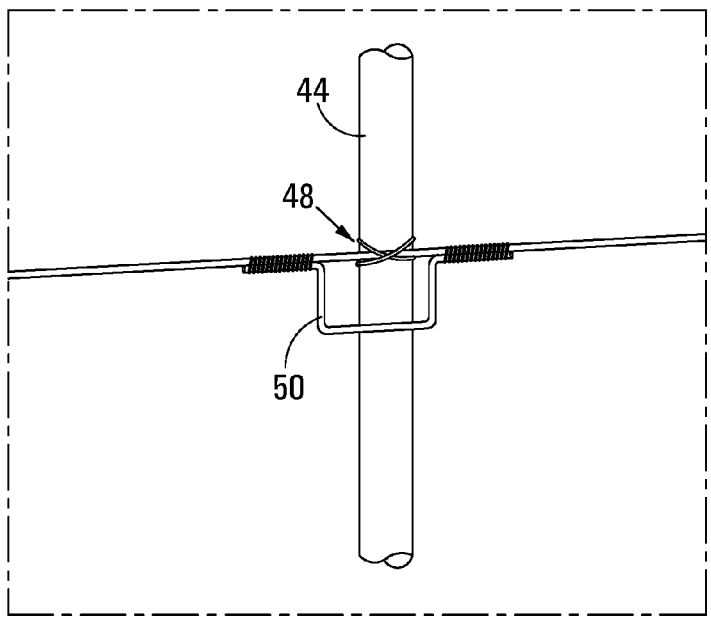
FIG. 4 shows part of a fence post and details a modification made to the fence in order to improve the range of the system.

The device 10, system 100 and method find application in the monitoring of tensioned cables 12 which make-up a fence, although the application is not limited to this particular use. When a person attempts to cut, loosen, climb through or dismantle the fence to gain unauthorised entry, acoustic waves caused through physical contact with the cables 12 are transmitted along the cables 12 and to the cable monitoring transducer 14.1 via the coupler 16. This differential-mode signal is in turn amplified by the amplifier 17 while the common-mode signal is rejected. If the amplified output 17.3 exceeds a predefined threshold the alarm is triggered. In order to prevent attenuation of the acoustic waves and to increase an operating range of the device 10, fixation points 48 (see FIG. 4) where the cable 12 is attached to the fence post 44 is bridged using a bridging element 50, for example, a length of wire which is attached to the cable 12 on either side of the post 44. In this manner an acoustic wave travelling along the cable 12 can pass along the bridging element 50 instead of terminating, or at least attenuating at the fixation point 48.

Figure 5:
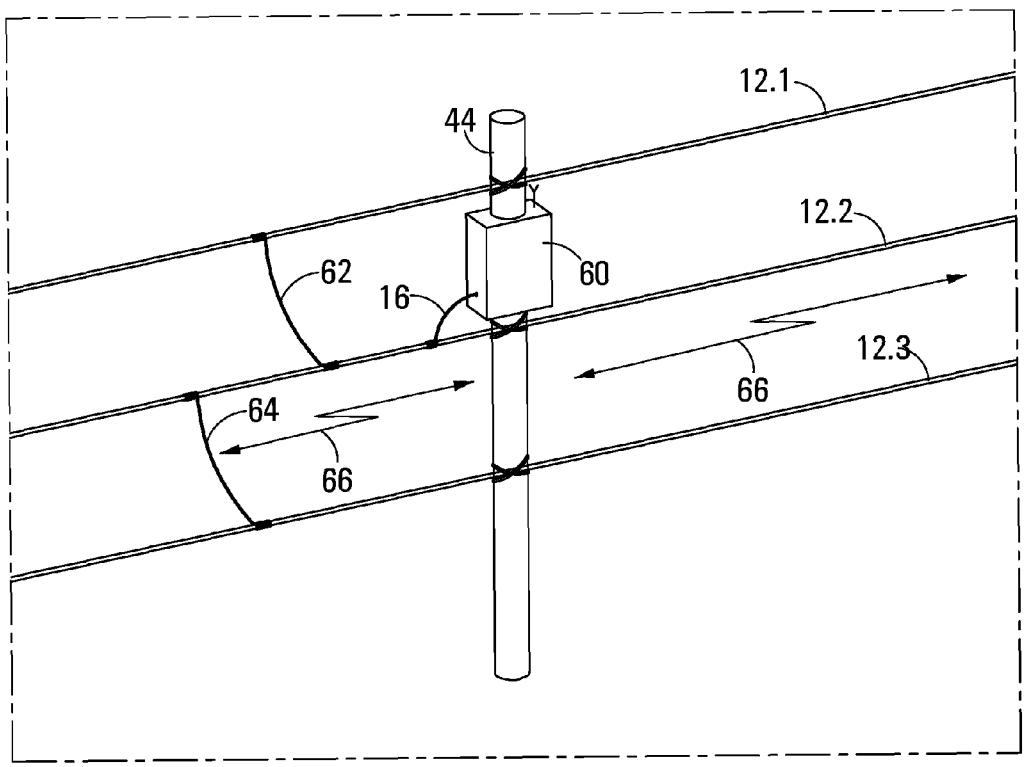
FIG. 5 shows a diagrammatic illustration of the system in accordance with a second embodiment of the invention.

As best shown in FIG. 3, each cable 12 has a device 10 fitted thereto with a coupler 16. Alternatively, with reference now to FIG. 5, one device 60 may be arranged to monitor a plurality of cables 12.1, 12.2, 12.3, in which case the cable monitoring transducer (not shown, but similar to transducer 14.1 described above) in the device 60 is connected to the plurality of cables 12.1, 12.2 and 12.3 with a plurality of couplers 16, 62 and 64, respectively. The device 60 includes the components and circuitry of device 10 (as shown in FIG. 1), and thus operates substantially similarly. However, the device 60 further includes a control module (similar to control module 30 described above), a communication module (similar to communication module 40 described above), and a battery. Again, the operation of the control module and the communication module is substantially as described above. In particular, the device may communicate with adjacent devices 60, and ultimately a remote monitoring station, using RF communication, as indicated by arrows 66 in FIG. 5.

The device 10, 60 and/or system 100 may further include a mechanical strain gauge (not shown) mounted to the cable 12, the gauge being configured to sense a change in tension in the cable 12, for example, when adjacent cables 12 are separated to climb through the fence and in response thereto to generate a mechanical wave or acoustic wave in the cable 12 which may trigger the alarm provided the wave exceeds the threshold value.

The device 10, 60 can be fitted as shown in the attached drawings, but it can be fitted onto practically any structure, including walls. In one particular version, the acoustic conductor being monitored by the device 10, 60 is the ground, the purpose of which is to determine whether someone is digging a hole in the ground. In this version, the device 10, 60 is fitted to a peg inserted into the ground, with the acoustic conductor monitoring transducer being in acoustic contact with the ground. The operation of the device 10, 60 is, however, substantially as described above.

In yet a further embodiment, the acoustic conductor comprises an irrigation pipe. In this version, the aim of the present invention is to protect against tampering and/or theft of sprinkler heads, but, again, the operation of the device 10, 60 is substantially as described above.

In an embodiment, the device 10, 60 may include a pair of acoustic conductor monitoring transducers 14.1 fitted to the same cable 12 and a pair of corresponding ambient transducers 14.2. As is relatively well known, the pair of acoustic conductor monitoring transducers 14.1 may be spaced one wavelength ($1\lambda$) apart from each other and/or the pair of ambient transducers may be spaced one wavelength ($1\lambda$) apart from each other, to reinforce these signals. Conversely, the pair of acoustic conductor monitoring transducers 14.1 and the pair of ambient transducers 14.2 may be spaced a half wavelength ($\frac{1}{2}\lambda$) apart from each other, to attenuate the signals between the monitoring transducers 14.1 and the ambient transducers 14.2. In this embodiment, the circuit element comprises a passive amplifier to amplify the resulting differential signal.

In a similar arrangement, when using piezoelectric transducers in particular, the piezoelectric transducers may be connected together so as to reinforce the signals from the monitoring transducers 14.1 and/or ambient transducers 14.2, and to attenuate the signals between the monitoring transducers 14.1 and ambient transducers 14.2, with the circuit element comprising a passive amplifier to amplify the resulting differential signal.

In the arrangements described in the preceding two paragraphs, there is no need for a differential amplifier.

Before activating the system 100 of the present invention, a sonar signal may be sent down the cable 12, to check whether the cable 12 has been tampered with. After tampering (or potential tampering) has been detected, a follow up sonar signal may be sent down the cable, which may then be compared to the sonar before the tampering (or potential tampering).

In the context of a typical fence arrangement, the system 100 may include a gate having a sensor to determine whether the gate is opening or is open. A bell or buzzer may be fitted proximate the gate, which upon being pressed, notifies a person who may then decide whether or not to open the gate.

In one envisaged implementation, the device 60 may be used to monitor a 100 meter stretch of fence. As indicated above, each cable or strand would be monitored by a single device 60. Each device may be assigned a unique 8 bit identifier, and thus an entire system 100 may typically manage around 250 devices 60. This in turn means that a system 100 can monitor and protect 25 kilometers of fence. Each device 60 operates using 2 AA batteries, and will on average draw 50 uA of current. In one particular application, the remote monitoring station may take the form of a handheld device, which may be programmed with the unique 8 bit identifiers (and GPS position) of each device 60. The handheld device may either be a basic telephone, in which an alarm trigger (and details of the particular device 60) is sent as an SMS to the handheld device. Alternatively, the handheld device may take the form of a smart phone (or even a tablet), which can display, for example, a map of the area and identify the position of the relevant device 60. Furthermore, the system 100 may include an remote controlled, unmanned aircraft which is configured to fly out the position where a disturbance has been detected in order to perform surveillance. Accordingly, the aircraft may include surveillance equipment in the form of a video camera etc.

The device 10, 60 and system 100 in accordance with the invention for monitoring a cable for a physical disturbance is fairly simple which makes it very cost effective. Installation of the device 10, 60 and/or system 100 is straightforward and does not require technical expertise. The device 10, 60 is retrofittable to any existing tensioned cable or wire irrespective of its purpose or function. In general, little to no modification to an existing fence is required to mount the device 10, 60 and no penetration of the cable is necessary. Some fencing arrangements have cables or strands that extend transversely (as opposed to straight along, substantially parallel to the ground). In such a case, it may be necessary to fit a straight cable to the transversely extending cables, to which the device 10, 60 may then be fitted.

The Inventor believes that the proposed device 10, 60 and system 100 addresses some of the drawbacks associated with existing cable monitors.

The invention claimed is:

1. A device for monitoring an acoustic conductor for a physical disturbance, the device including:
    at least one pair of acoustic transducers, the pair comprising a first acoustic conductor monitoring transducer and a second ambient transducer, the first acoustic conductor monitoring transducer operatively being in acoustic contact with the acoustic conductor to be monitored by the device, the second ambient transducer being isolated from the acoustic conductor and hence from the physical disturbance on the acoustic conductor, the second ambient transducer not being in acoustic contact with the acoustic conductor such that the physical disturbance conveyed to the first acoustic conductor monitoring transducer is not conveyed to the second ambient transducer, the transducers being arranged such that an ambient acoustic signal is common to both transducers;
    a circuit element, with each transducer being connected to an input of the circuit element, the circuit element being arranged to cancel the ambient acoustic signal common to both transducers and to output an output signal which is a difference between input signals received from the first acoustic conductor monitoring transducer and the second ambient transducer, respectively; and
    an alarm triggering module which is connected to an output of the circuit element, the module being operable to trigger an alarm when the output signal received from the circuit element exceeds a predefined threshold value, wherein the acoustic transducers are arranged in close proximity to each other to ensure that the ambient acoustic signal is common to both transducers.

2. The device of claim 1, wherein the acoustic conductor comprises a cable, the first acoustic conductor monitoring transducer being a cable monitoring transducer.

3. The device of claim 2, wherein the device includes a coupler which operatively connects the cable to be monitored to, or brings the cable in abutment with, the cable monitoring transducer such that a mechanical wave or vibration in the cable is transferred or conveyed to the cable monitoring transducer.

4. The device of claim 3, wherein the device is configured to monitor a plurality of cables, in which the cable monitoring transducer in the device is connected to the plurality of cables with a plurality of couplers.

5. The device of claim 1, wherein the circuit element comprises a differential amplifier, wherein each transducer is connected to an input of the amplifier, which is configured to cancel a signal common to the inputs thus amplifying and outputting a difference between the input signals received from the first acoustic conductor monitoring transducer and the second ambient transducer, respectively.

6. The device of claim 5, wherein the device includes a high pass filter connected between each transducer and an input to the circuit element.

7. The device of claim 1, wherein the alarm triggering module includes at least one comparator having a predefined threshold voltage as one input to the comparator and the output of the circuit element as the other input, so that when the output received from the circuit element exceeds the predefined threshold voltage, the comparator is configured to trigger an alarm.

8. The device of claim 1, wherein the alarm triggering module includes an analogue-to-digital converter (A/D) and a processor which is operable to compute, based on a level of the output received from the circuit element, whether or not the alarm should be triggered and to trigger the alarm depending on an outcome of the computation.

9. The device of claim 1, wherein the device further includes a communication module connected to the alarm triggering module, the communication module being operable to communicate with a remote monitoring station.

10. The device of claim 1, wherein the acoustic transducers are in the form of microphones.

11. The device of claim 1, wherein the acoustic transducers are in the form of piezoelectric transducers.

12. The device of claim 9, wherein the first acoustic conductor monitoring transducer is configured to be arranged in direct mechanical contact with the acoustic conductor being monitored.

13. The device of claim 2, wherein the cable is an electrified cable, the device being resistant to electrical shock.

14. The device of claim 1, wherein the acoustic conductor comprises a ground, in which case the device is fitted to a peg inserted into the ground, with the first acoustic conductor monitoring transducer being in acoustic contact with the ground.

15. A method of monitoring a cable for a physical disturbance, the method including:
    placing a first acoustic transducer in acoustic contact with the cable to be monitored and measuring using the first acoustic transducer an acoustic signal associated with the cable;
    using the first acoustic transducer and a second acoustic transducer, simultaneously measuring an ambient acoustic signal which is common to the first and second acoustic transducers;
    cancelling using a circuit element the ambient acoustic signal which is common to the first and second transducers in order to amplify the acoustic signal associated with the cable; and
    triggering using an alarm triggering module an alarm or warning signal when an output signal received from the circuit element exceeds a predefined threshold value.

16. The method of claim 15, wherein the triggering step includes communicating via a communication module over a communication network, an occurrence of an alarm triggering event to a remote station.

17. A system for monitoring an acoustic conductor for a physical disturbance, the system including:
- at least one device for monitoring the acoustic conductor for the physical disturbance, the device including at least one pair of acoustic transducers, the pair comprising a first acoustic conductor monitoring transducer and a second ambient transducer, the first acoustic conductor monitoring transducer operatively being in acoustic contact with the acoustic conductor to be monitored by way of a coupler such that the first acoustic conductor monitoring transducer is able to measure an acoustic signal associated with the acoustic conductor, the second ambient transducer being isolated from the acoustic signal on the acoustic conductor by not being in acoustic contact with the acoustic conductor such that the acoustic signal conveyed to the first acoustic conductor monitoring transducer is not conveyed to the second ambient transducer, the transducers being arranged such that an ambient acoustic signal is common to both transducers, wherein the device is configured, through the use of a circuitry, to cancel the ambient acoustic signal common to both transducers and to output an output signal which is a difference between input signals received from the first acoustic conductor monitoring transducer and the second ambient transducer, respectively, wherein the acoustic transducers are arranged in close proximity to each other to ensure that the ambient acoustic signal is common to both transducers; and
- a control module which is in communication with the device and which is configured to receive as an input, the output signal of the circuitry of the device, the control module being operable to determine, based on the output signal received from the device whether or not an alarm triggering event has occurred, and to trigger an alarm if need be.

18. The system of claim 17, wherein the control module is operable to receive as inputs, output signals of circuitry of at least two separate devices and wherein the control module is operable to calculate a location of a physical disturbance measured between the two devices connected to the same acoustic conductor, the two devices being a predetermined distance apart.

19. The system of claim 17, which includes a remote monitoring station in the form of a handheld unit comprising a GPS, the device further including a communication module which is configured to communicate with the handheld unit and to forward a notification message to the handheld unit in the event that the alarm is triggered.

* * * * *